United States Patent [19]
Hageman

[11] Patent Number: 5,389,088
[45] Date of Patent: Feb. 14, 1995

[54] GROMMET

[76] Inventor: Marinus J. Hageman, Anna van Burenlaan 3, 2012 SL Haarlem, Netherlands

[21] Appl. No.: 976,101

[22] Filed: Nov. 13, 1992

[30] Foreign Application Priority Data

Nov. 14, 1991 [NL] Netherlands ............. 9101898

[51] Int. Cl.⁶ .............................................. A61M 27/00
[52] U.S. Cl. ...................................... 604/264; 604/284
[58] Field of Search ................. 604/93, 264, 280, 26, 604/175; 606/188; 623/10–12

[56] References Cited

U.S. PATENT DOCUMENTS

| | | | |
|---|---|---|---|
| 3,818,511 | 6/1974 | Goldberg et al. | 623/12 |
| 3,871,380 | 3/1975 | Heros | 604/264 |
| 4,650,488 | 3/1987 | Bays | 623/12 |
| 4,695,275 | 9/1987 | Bruce et al. | 604/264 |
| 4,775,370 | 10/1988 | Berry | 604/264 |
| 4,808,171 | 2/1989 | Berger | 604/264 |
| 5,064,417 | 11/1991 | Andreussi | 604/175 |
| 5,137,523 | 8/1992 | Peerless et al. | 604/264 |
| 5,139,502 | 8/1992 | Berg et al. | 604/264 |

FOREIGN PATENT DOCUMENTS 1368758 10/1974 United Kingdom .

*Primary Examiner*—C. Fred Rosenbaum
*Assistant Examiner*—Chalin Smith
*Attorney, Agent, or Firm*—Young & Thompson

[57] ABSTRACT

A grommet at one side comprises a tubular part which widens out either in a regular trumpet-shaped curve ("monotonic") or via one or more "steps" or "bends" with the result that the risk of blockage is considerably reduced and the grommet is less quickly expelled from the eardrum. At the other side, the grommet is provided with a flange via which the grommet remains hooked behind the eardrum. This flange is so large - either round and the same size as the widely "fanning" top side of the trumpet-shaped top part of the grommet, or provided with one or more symmetrical or asymmetrical projections - that the grommet is held fast by the eardrum for a relatively long time. A recurrence of the fluid accumulation in the tympanic cavity or of an ear infection is consequently less likely to occur.

8 Claims, 3 Drawing Sheets

GROMMET

FIELD OF THE INVENTION

The invention relates to a grommet, comprising a tubular part at one end and at the other end an external flange which can be hooked behind the internal surface of the eardrum.

BACKGROUND OF THE INVENTION

Grommets have become the most common implants in the human body in recent years. The insertion of grommets has now become the most common form of operation, not only in the ENT field, but also in all branches of surgery in the North Western part of the world (Europe and the United States); that is why it is of great importance to design grommets which are better than those currently being used.

Grommets are known in many forms. In this connection reference is made to the thesis entitled "Trommelvliesbuisjes" (Grommets), W. H. Moesker, Amsterdam, 1991, which gives a general description of all kinds of grommets. Most of them are in the form of a "collar-button". They have a "waist"-shaped middle part, which makes the grommet sit securely in the eardrum after a hole has been made in the eardrum. Since the material of the eardrum is slightly elastic, it can be stretched during insertion of the grommet, and will spring back after the grommet is in its correct position.

The purpose of grommets is to provide the tympanic cavity with air, in order to relieve hardness of hearing due to moisture in the tympanic cavity as a result of little or no ventilation of the tympanic cavity. The fact that there is little or no ventilation produces partial vacuum in the tympanic cavity, with the result that fluid is sucked out of the mucous membrane lining the tympanic cavity. The tympanic cavity is thus filled with fluid (otitis media serosa), which gives rise to hardness of hearing and a greatly increased risk of ear infections. This partial vacuum occurs through the fact that the mucous membrane lining the Eustachian tube is swollen as a result of a runny nose and cold, which is particularly common in children.

The disadvantage of the current grommets is that they soon become blocked with congealed fluid, mucus or blood from the tympanic cavity, or by ear wax. They are therefore no longer able to fulfil their function of ventilation of the tympanic cavity. Besides, a grommet which is blocked is more quickly expelled through the formation of fluid and mucus in the tympanic cavity, which, as it were, pushes out the grommet.

A number of the most commonly used grommets are mentioned below, with their specific disadvantages:

The Shepard grommet. Disadvantages: The grommet quickly becomes blocked through the relatively long and straight tubular channel and the presence of a neck. As a result, the grommet is expelled relatively quickly from the eardrum. The absence of a genuine flange means that the grommet is expelled particularly quickly. Moreover, the grommet is difficult to insert with fine insertion forceps, due to the awkwardly shaped, thick top side of the grommet.

The collar-button grommet in the shape of a diabolo. This grommet also quickly becomes blocked owing to the straight, tubular channel, with the result that it too is expelled relatively quickly. The diabolo shape means that this grommet easily fits completely under the eardrum.

The "Donaldson" grommet. This grommet is more or less the same diabolo shape as the collar-button grommet, and thus has the same disadvantages. It also has another disadvantage: the small dimensions of the flange which goes under the eardrum means that this grommet remains on average an even shorter time in position than the collar-button grommet.

The LENS grommet. The relatively long neck between the flange at the bottom side and the funnel-shaped top side means that this grommet also quickly becomes blocked and is expelled as a result.

There are also many other grommets which are less often used.

If a grommet is expelled quickly from the eardrum (for example, after 6 months or sooner), there is more than a 50% chance of a recurrence of fluid accumulation in the tympanic cavity and of an ear infection occurring, which makes another insertion (generally under general anaesthetic) of a grommet necessary. If, on the other hand, a grommet remains longer in the eardrum (between one and two years), the chance of a recurrence of fluid accumulation in the tympanic cavity and of ear infections is reduced to below 50%. A grommet thus has an ideal residence time of one to two years.

The residence time of the grommet is determined by:
a. the angle which the tubular part forms with the flange which hooks under the eardrum;
b. the size and shape of the flange.

Re: a. the angle between tubular part and flange: If this angle is small and is not acute, but is obtuse, that is to say more than 90 degrees (as in the case of the Shepard grommet), the residence time of the grommet will be short. The more acute this angle, that is to say 90° or less, the longer the grommet will, as it were, remain hooked under the eardrum.

Re: b. the size and shape of the flange: If the flange is relatively small (as in the case of the Donaldson grommet), the residence time will be relatively short.

The above-mentioned grommets belong to the group of grommets which remain a relatively short time in the eardrum, from several months to many months.

In addition, there is a group of grommets which remain for a very long time in the eardrum, in general many years. The most well-known of this group is the T-drain, also called after its inventor Goode: the Goode T-drain. These grommets, which stay in the eardrum for many years, have not only the advantage of a long residence time, but also the disadvantage that their long residence time in many cases gives rise to permanent holes in the eardrum, which have to be closed surgically.

Since many millions of grommets are placed annually, slight differences (in quality) between them can have great consequences (in quantity).

SUMMARY OF THE INVENTION

The object of the invention is to provide a grommet which does not have the above-mentioned disadvantages, i.e. does not become blocked quickly and remains in place in the eardrum for a relatively long time, but not too long (on average two years), so that there is less chance of a rapid recurrence of fluid accumulation and ear infection and another grommet does not have to be implanted again soon (under general anaesthetic).

This object is achieved, on the one hand, through the fact that the tubular part of the grommet widens out in a trumpet shape from the flange and, on the other, through the special shape and size of the flange with which the grommet hooks under the eardrum. The trumpet-shaped widening of the top side means that this grommet can be gripped easily between the relatively fine jaws of forceps. The Shepard grommet is found to be considerably less advantageous in this respect, since the part to be gripped with the forceps is quite thick. The LENS grommet, which has a tubular part with a widened end piece with a large apex angle, is also found to be less good in this respect.

The trumpet-shaped widening of the passage means that the grommet has little or no cylindrical part such as is the case in the known grommets. It is therefore much less likely that any pollutants will become lodged in the interior passage of the grommet. In this connection it is important for the trumpet-shaped widening of the passage to be in principle self-discharging, in other words, any pollutant cannot become lodged in the passage.

A further advantage of the grommet according to the invention lies in the fact that the eardrum wall can be held well confined between the flange and the widening tubular part directly connecting to it. This ensures that the grommet cannot slide to and fro along its axis, which reduces the risk of premature detachment.

The internal opening in the grommet must not be too large, given the problems which can occur if moisture penetrates into the middle ear. On the other hand, this opening must not be too small either, otherwise it would too easily become blocked, and air would no longer be able to flow through it. The known grommets have a cylindrical passage, the internal diameter of which is around 1 mm. The longer this passage, the greater is the risk of blockages. Since in the case of the invention the entire tubular part is widened in a funnel shape, the passage has the minimum measurement of, for example, 1 mm only at the position of the flange. This ensures, on the one hand, a good seal against the penetration of moisture, while on the other hand the chance of blockages is relatively small.

In order to make the residence time of the grommet of this invention in the eardrum relatively long, the present grommet is designed as follows:
  a. the angle between the flange and the trumpet-shaped top side is smaller than 90°.
  b. the flange is relatively large, namely either round and the same size as the widely "fanning" top side of the trumpet-shaped top part of the grommet, or is provided with one or more symmetrical or asymmetrical "projections";
  c. there is no neck, which is present in, for example, the Shepard grommet, the collar-button grommet, the Donaldson grommet and the LENS grommet.

The grommet according to the invention can be designed in various ways. According to a first possible embodiment, the part projecting above the flange is trumpet-shaped, in other words it widens out in a regular monotonically curved shape from the flange.

The second possibility is that the tubular part widens out in a trumpet shape by means of "bends". The first tubular part connecting to the flange is followed by one or more following tubular parts whose apex angle(s) is (are) greater than that (those) of the preceding part(s).

The flange of the grommets according to the above two possibilities is relatively large, namely the same size as the widely "fanning" top side of the trumpet-shaped top part, and either round or the flange has one or more symmetrical or asymmetrical projections.

In all these embodiments the wall thickness of the tubular part is constant. The grommet can be gripped in a very suitable manner on the wall of the tubular part by fine forceps. The relatively wide opening of the tubular part provides the necessary space for placing the forceps, while the limited diameter of the passage near the flange still provides good protection against any penetrating moisture.

Needless to say, the tubular part can also be made conical, as known from, for example, U.S. Pat. No. 4,775,370.

BRIEF DESCRIPTION OF THE DRAWINGS

The invention will be explained in greater detail below with reference to the examples of embodiments.

DETAILED DESCRIPTION OF THE INVENTION

Figure 1:
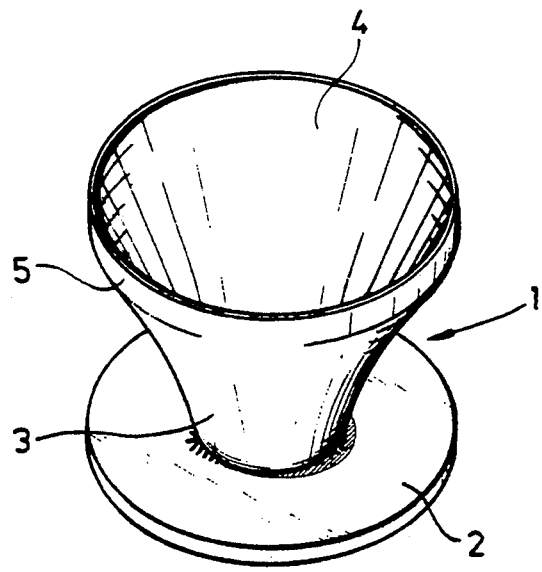
FIG. 1 shows a first embodiment of the grommet according to the invention, in perspective.

The grommet shown in FIG. 1 has a flange 2, to which a tubular part 3 is connected. This tubular part widens in a trumpet-shape from the flange 2. The internal passage 4 in the tubular part 3 narrows increasingly in the direction of the flange 2, and has an opening at the position of said flange 2 with a diameter of, for example, 1 mm. Its end with the largest diameter through the tubular part 3 may, if desired, have a thickened edge 5.

Figure 2:
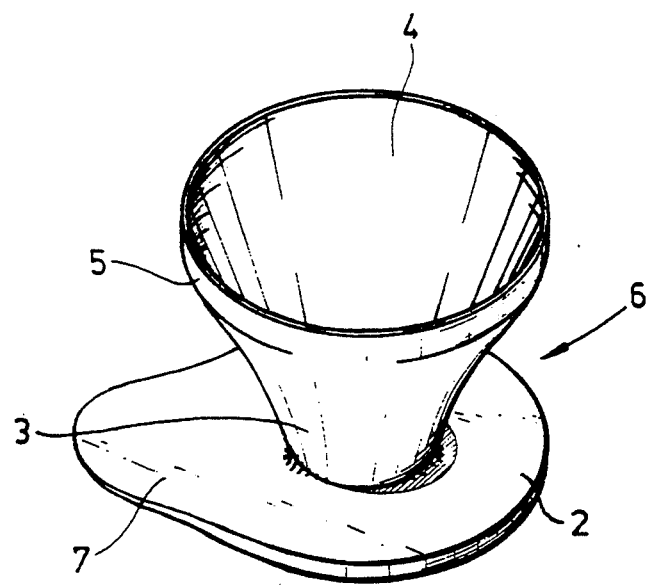
FIG. 2 shows a second embodiment.

The embodiment of the grommet 6 shown in FIG. 2 differs from the grommet shown in FIG. 1 only in the shape of the flange part; the flange part has a projection 7.

Figure 3:
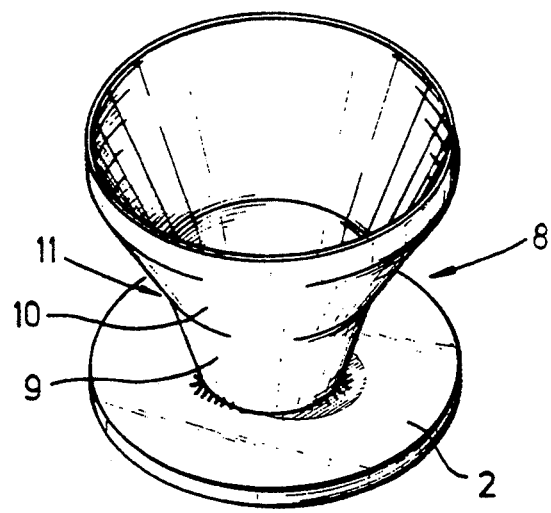
FIG. 3 shows a third embodiment.

The embodiment of the grommet 8 shown in FIG. 3 differs from the grommets of FIGS. 1 and 2 only in the shape of the tube; connecting to the flange 2 is a conically widened part 9, to which, in turn, a second conically widened part 10 connects. Both parts 9 and 10 form the tubular part 11 of the grommet 8. The apex angle of the conically widened part 10 is slightly larger than that of the conically widened part 9. This, on the one hand, produces a fairly large opening of the grommet 8, in such a way that it can easily be gripped with fine forceps. On the other hand, the first part 9 of the tubular part 11 has a relatively narrow passage, which has the smallest measurement, for example 1 mm, near the flange. This again ensures good protection from any penetrating moisture.

Figure 4:
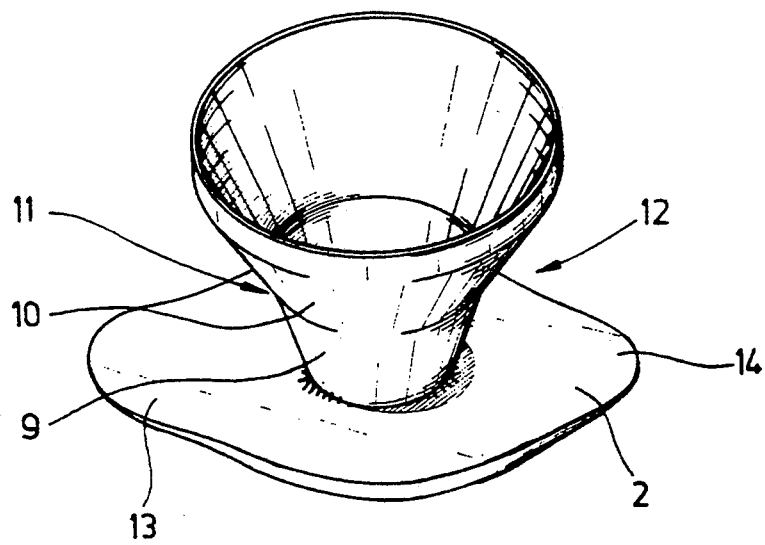
FIG. 4 shows a fourth embodiment.

FIG. 4 shows the grommet 12, which differs from FIG. 3 only in the flange part. The flange part has 2 projections which are not identical (asymmetrical); one projection 13 is slightly larger than the other projection 14.

Figure 5:
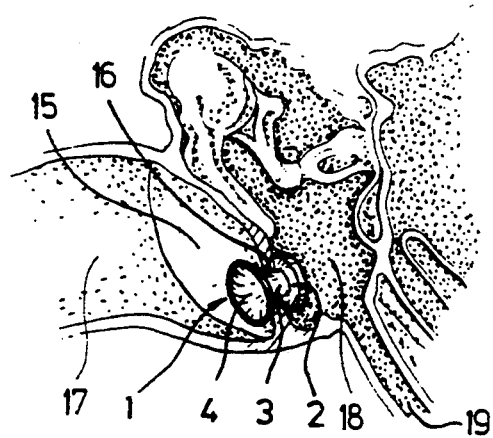
FIG. 5 shows a cross-section of the middle ear, in which the grommet according to FIG. 1 is placed in the eardrum.

FIG. 5 shows the grommet 1, placed in the partially cut-away eardrum 15. It can be seen that at the position of the hole 16 made in the eardrum 15, the eardrum 15 is held well between the flange 2 and the adjacent widening part of the tubular part 3. This ensures that the grommet is held well in the eardrum 15.

The grommet ensures that air can come out of the auditory meatus 17 to the tympanic cavity 18 if the Eustachian tube 19, which normally provides for ventilation of the tympanic cavity, is blocked.

I claim:

1. Grommet, comprising a tubular part which at one end is provided with an external flange sized to be hooked behind the internal surface of an eardrum, said tubular part widening out from the flange toward its free end, and said free end defining a cone having an apex angle which is larger than the apex angle of a cone which is defined by the end near the flange.

2. Grommet according to claim 1, wherein the tubular part is trumpet-shaped.

3. Grommet according to claim 1, wherein the tubular part further comprises a first conical part connecting to the flange, and a second conical part connecting to said first conical part, and the apex angle of said second conical part is greater than that of the first conical part.

4. Grommet according to claim 2, wherein the tubular part has a constant wall thickness.

5. Grommet according to claim 1, wherein the flange bears at least one projection.

6. Grommet according to claim 5, wherein the flange bears two projections which are disposed symmetrically relative to the central axis of the grommet.

7. Grommet according to claim 6, wherein one projection projects further than the other.

8. Grommet according to claim 5, wherein said at least one projection has a thickness which decreases in the direction of its end.

* * * * *